United States Patent
Cheng (10) Patent No.: US 10,624,607 B2
(45) Date of Patent: Apr. 21, 2020

(54) METHOD FOR GUIDING THE INSERTION OF A SURGICAL INSTRUMENT WITH THREE DIMENSIONAL ULTRASONIC IMAGING

(75) Inventor: Jeanne Cheng, Andover, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 882 days.

(21) Appl. No.: 13/884,172

(22) PCT Filed: Nov. 15, 2011

(86) PCT No.: PCT/IB2011/055082
§ 371 (c)(1),
(2), (4) Date: May 8, 2013

(87) PCT Pub. No.: WO2012/066470
PCT Pub. Date: May 24, 2012

(65) Prior Publication Data
US 2013/0225984 A1    Aug. 29, 2013

Related U.S. Application Data

(60) Provisional application No. 61/415,655, filed on Nov. 19, 2010.

(51) Int. Cl.
*A61B 8/00*    (2006.01)
*A61B 8/08*    (2006.01)
(Continued)

(52) U.S. Cl.
CPC ............ *A61B 8/463* (2013.01); *A61B 8/0841* (2013.01); *A61B 8/483* (2013.01); *A61B 8/523* (2013.01);
(Continued)

(58) Field of Classification Search
None
See application file for complete search history.

(56) References Cited

U.S. PATENT DOCUMENTS

| 5,095,910 A | 3/1992 | Powers |
| 5,158,088 A | 10/1992 | Nelson et al. |

(Continued)

FOREIGN PATENT DOCUMENTS

| EP | 2147636 A1 | 1/2010 |
| JP | 2003019133 A | 1/2003 |

(Continued)

OTHER PUBLICATIONS

PCT International Search Report, International application No. PCT/IB2011/055082, Apr. 2, 2012.

(Continued)

*Primary Examiner* — Oommen Jacob (57) ABSTRACT

The insertion of a needle or other surgical instrument into the body is guided by three dimensional ultrasonic imaging. A probe having a two dimensional array transducer is placed against the body and manipulated to acquire an image of the site of the surgical procedure inside the body. The clinician inserts the surgical instrument, trying to follow an insertion path which is in the plane of a single image produced by the ultrasound system. The clinician observes the path of insertion and insertion progress on a display of a plurality of real-time 2D ultrasound images of spatially adjacent planes of a volume including the surgical procedure site. If the insertion path of the instrument does not remain in the plane of a single image, portions of the instrument will appear in the images of multiple adjacent image planes when the instrument intersects a succession of image planes as it progresses toward the site of the surgical procedure.

22 Claims, 4 Drawing Sheets

(51) Int. Cl.
  *G01S 7/52*    (2006.01)
  *A61B 90/00*   (2016.01)
  *G01S 15/89*   (2006.01)
  *G06T 19/00*   (2011.01)
  *A61B 17/34*   (2006.01)

(52) U.S. Cl.
  CPC .......... *A61B 90/37* (2016.02); *G01S 7/52074* (2013.01); *G01S 15/8993* (2013.01); *G06T 19/00* (2013.01); *A61B 2017/3413* (2013.01); *A61B 2090/378* (2016.02); *G06T 2210/41* (2013.01); *G06T 2219/028* (2013.01)

(56) References Cited

U.S. PATENT DOCUMENTS

| | | | |
|---|---|---|---|
| 5,759,154 A * | 6/1998 | Hoyns | A61B 8/0833 |
| | | | 29/DIG. 16 |
| 5,786,693 A * | 7/1998 | Gullapalli | G01R 33/4835 |
| | | | 324/306 |
| 5,808,735 A * | 9/1998 | Lee | G01N 21/9501 |
| | | | 250/559.42 |
| 5,864,362 A * | 1/1999 | Cutler | H04N 1/126 |
| | | | 348/96 |
| 5,997,479 A | 12/1999 | Savord et al. | |
| 6,013,032 A | 1/2000 | Savord | |
| 6,283,919 B1 | 9/2001 | Roundhill et al. | |
| 6,443,896 B1 | 9/2002 | Detmar | |
| 6,458,083 B1 | 10/2002 | Jago et al. | |
| 6,530,885 B1 | 3/2003 | Entrekin et al. | |
| 6,572,547 B2 | 6/2003 | Miller et al. | |
| 6,572,549 B1 * | 6/2003 | Jong | A61B 8/08 |
| | | | 128/916 |
| 6,623,432 B2 | 9/2003 | Powers et al. | |
| 6,735,271 B1 * | 5/2004 | Rand | A61B 6/032 |
| | | | 378/15 |
| 6,748,347 B1 * | 6/2004 | Dalton | G06T 15/08 |
| | | | 345/426 |
| 7,177,486 B2 * | 2/2007 | Stewart | G06T 3/0081 |
| | | | 382/294 |
| 7,405,564 B2 * | 7/2008 | Harvey | G01R 33/5611 |
| | | | 324/307 |
| 7,529,393 B2 | 5/2009 | Peszynski et al. | |
| 2001/0044576 A1 * | 11/2001 | Vining | G06T 7/0012 |
| | | | 600/416 |
| 2003/0007598 A1 * | 1/2003 | Wang | A61B 6/463 |
| | | | 378/37 |
| 2003/0174872 A1 * | 9/2003 | Chalana | G06K 9/00 |
| | | | 382/128 |
| 2004/0199064 A1 * | 10/2004 | Van Liere | G06T 11/005 |
| | | | 600/407 |
| 2005/0255136 A1 | 11/2005 | Fleissman et al. | |
| 2006/0025673 A1 * | 2/2006 | De Leon | G06T 7/0012 |
| | | | 600/410 |
| 2006/0114254 A1 * | 6/2006 | Day | G06T 15/08 |
| | | | 345/424 |
| 2007/0100234 A1 * | 5/2007 | Arenson | A61B 6/032 |
| | | | 600/429 |
| 2007/0255136 A1 | 11/2007 | Kristoferson et al. | |
| 2007/0255139 A1 | 11/2007 | Deschinger et al. | |
| 2008/0247635 A1 * | 10/2008 | Davis | G06T 19/00 |
| | | | 382/152 |
| 2009/0024039 A1 * | 1/2009 | Wang | A61B 10/0233 |
| | | | 600/459 |
| 2009/0131790 A1 * | 5/2009 | Munrow | A61B 8/0841 |
| | | | 600/439 |
| 2009/0306511 A1 * | 12/2009 | Yamagata | A61B 8/0833 |
| | | | 600/447 |
| 2010/0121190 A1 | 5/2010 | Pagoulatos et al. | |
| 2010/0168580 A1 | 7/2010 | Thiele | |
| 2010/0240997 A1 * | 9/2010 | Ichioka | A61B 8/00 |
| | | | 600/443 |
| 2010/0268067 A1 | 10/2010 | Razzaque et al. | |
| 2010/0312117 A1 * | 12/2010 | Fernandez | A61B 8/0833 |
| | | | 600/458 |

FOREIGN PATENT DOCUMENTS

| | | |
|---|---|---|
| JP | 2003190165 A | 7/2003 |
| JP | 2005323669 A | 11/2005 |
| JP | 2006130162 A | 5/2006 |
| JP | 2007236767 A | 9/2007 |
| JP | 2009147620 A | 7/2009 |
| WO | 2009044316 A1 | 4/2009 |

OTHER PUBLICATIONS

Sites et al., "Characterizing Novice Behavior Associated With Learning Ultrasound-Guided Peripheral Regional Anesthesia", Regional Anesthesia and Pain Medicine, vol. 32, No. 2, pp. 107-115, Mar.-Apr. 2007.

* cited by examiner

FIG. 4

METHOD FOR GUIDING THE INSERTION OF A SURGICAL INSTRUMENT WITH THREE DIMENSIONAL ULTRASONIC IMAGING

This invention relates to ultrasonically guided invasive procedure and, in particular, to invasive procedures guided by three dimensional ultrasonic imaging.

Figure 4:
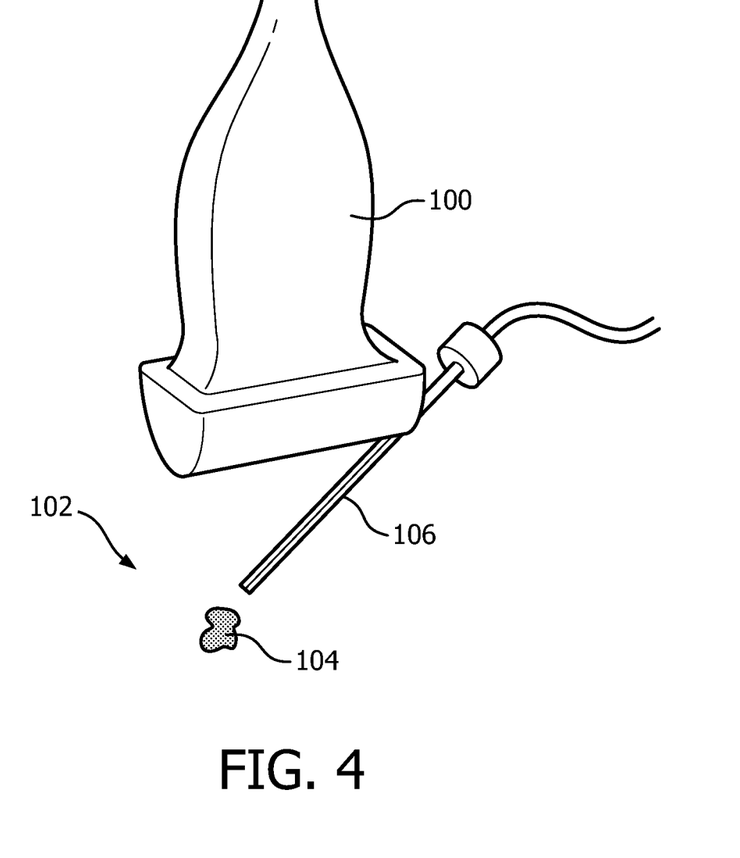
FIG. 4 illustrates the introduction of a needle in the two dimensional image plane of an ultrasound probe.

A number of surgically invasive procedures can be guided by ultrasonic imaging, which displays the interior of the tissue which is the subject of the invasive procedure. Predominate among such procedures are those requiring needle guidance and targeting, such as biopsies of observed masses in the breast and regional anesthesia administration. In these procedures the target tissue can be visualized with ultrasound as well as the path of the needle as it passes through tissue toward the target tissue. A number of ultrasound imaging systems and devices have been developed for the performance of such procedures. When two dimensional (2D) ultrasound imaging is used, it is important to keep the needle aligned with the image plane. This is illustrated in FIG. 4, which shows an ultrasound probe 100 that scans a 2D image plane 102. The probe is positioned so that the target tissue 104 is visible in the image. The needle 106 accessing the target tissue 104 must continually travel in the image plane 102. If the needle travels out of the image plane it can no longer be visualized and observed as it approaches the target tissue. Biopsy guides are commercially available for many ultrasound probes which allow the needle to be introduced into the body only in the plane of the ultrasound image. Another technique for dealing with this requirement is described in U.S. Pat. No. 5,158,088 (Nelson et al.). In the Nelson et al. system, a transducer is located at the tip of the introducer stylet, which broadcasts a signal that is received by the ultrasonic imaging probe. This signal is received by the probe and used to develop an audible signal as the tip of the stylet approaches and then intersects the imaging plane. Signals received by the stylet transducer can be used to identify the tip of the stylet in the 2D ultrasound image. Another 2D imaging technique is described in U.S. Pat. No. 5,095,910 (Powers). The Powers system vibrates the stylet and this vibratory motion is detected by ultrasonic Doppler techniques. The color Doppler signal in the ultrasound image indicates the location of the tip of the stylet. But again, the stylet must be in the image plane in order for Doppler detection and imaging to occur.

Three dimensional (3D) ultrasonic imaging has shown promise in overcoming the 2D image plane alignment problem. Since 3D imaging images a volume of tissue and not just a single plane, the constraint of alignment with a single plane is avoided. But many clinicians are not familiar with 3D ultrasound or the appearance of anatomy in 3D ultrasonic images. In addition, surround tissue can obscure the target tissue, the needle in the imaged volume, or both. U.S. Pat. No. 7,529,393 (Peszynski et al.) shows several approaches to dealing with these difficulties, including displaying the tip of the needle with greater display line density, showing the needle tip in a smaller subvolume, and combining both 2D and 3D imaging in one display. Another way to use 3D imaging is to display three mutually orthogonal image planes which converge at the tip of the surgical instrument, as described in U.S. Pat. No. 6,572,547 (Miller et al.) and US Pat. pub. no. US2010/0121190. Yet a third way is described for computed tomography and CT fluoroscopy in US Pat. pub. no. US2007/0100234 (Arenson et al.) In the Arenson et al. system a fan beam of x-rays is projected toward several rows of detector elements. Each row of detectors is used to reconstruct an image, and all of the rows are used for multi-slice CT fluoroscopic imaging. When the needle passes through the tissue imaged by the multiple slices, the needle is detected in each image and the multiple images are combined to form a composite thick slice image shows all of the needle segments in all of the combined slice images. However the patient table or the gantry must be constantly adjusted to keep the target tissue in line between the x-ray source and the detectors. In addition, fluoroscopy exposes the patient and the operator to ionizing radiation. Accordingly it is desirable to provide an ultrasonic technique for surgical instrument guidance so as to avoid ionizing radiation. It is further desirable for the ultrasonic technique to avoid the problem of image plane and needle alignment that is faced by prior art techniques, and to provide a system that is simple to use and readily comprehended by those not well familiar with 3D ultrasound imaging.

In accordance with the principles of the present invention, an ultrasonic imaging system and method are described for guiding an invasive instrument such as a surgical needle to target tissue in the body. The system uses a probe with a two dimensional array of transducer elements which electronically steers beams in three dimensions so as to scan a volumetric region of the body in real time. The 2D array probe can be easily manipulated to acquire images of the target tissue and the path traveled by an invasive device to reach the target tissue, and to optimize the angle of incidence between the ultrasound beams and the instrument. The echoes received from three dimensions of tissue are processed by a multiplanar reformatter into a plurality of spatially adjacent 2D image planes. The images of the spatially adjacent planes are concurrently display in the sequence of their spatial order in the tissue and continually updated in real time. As the invasive device approaches the target tissue its passage can be followed from one image plane to the next, and the spatial order of the images gives the clinician an intuitive sense of the progress of the instrument travel. Adjacent images can overlap each other in the thickness dimension so that the needle can be seen in adjacent images simultaneously and its insertion progress more easily followed.

Figure 1:
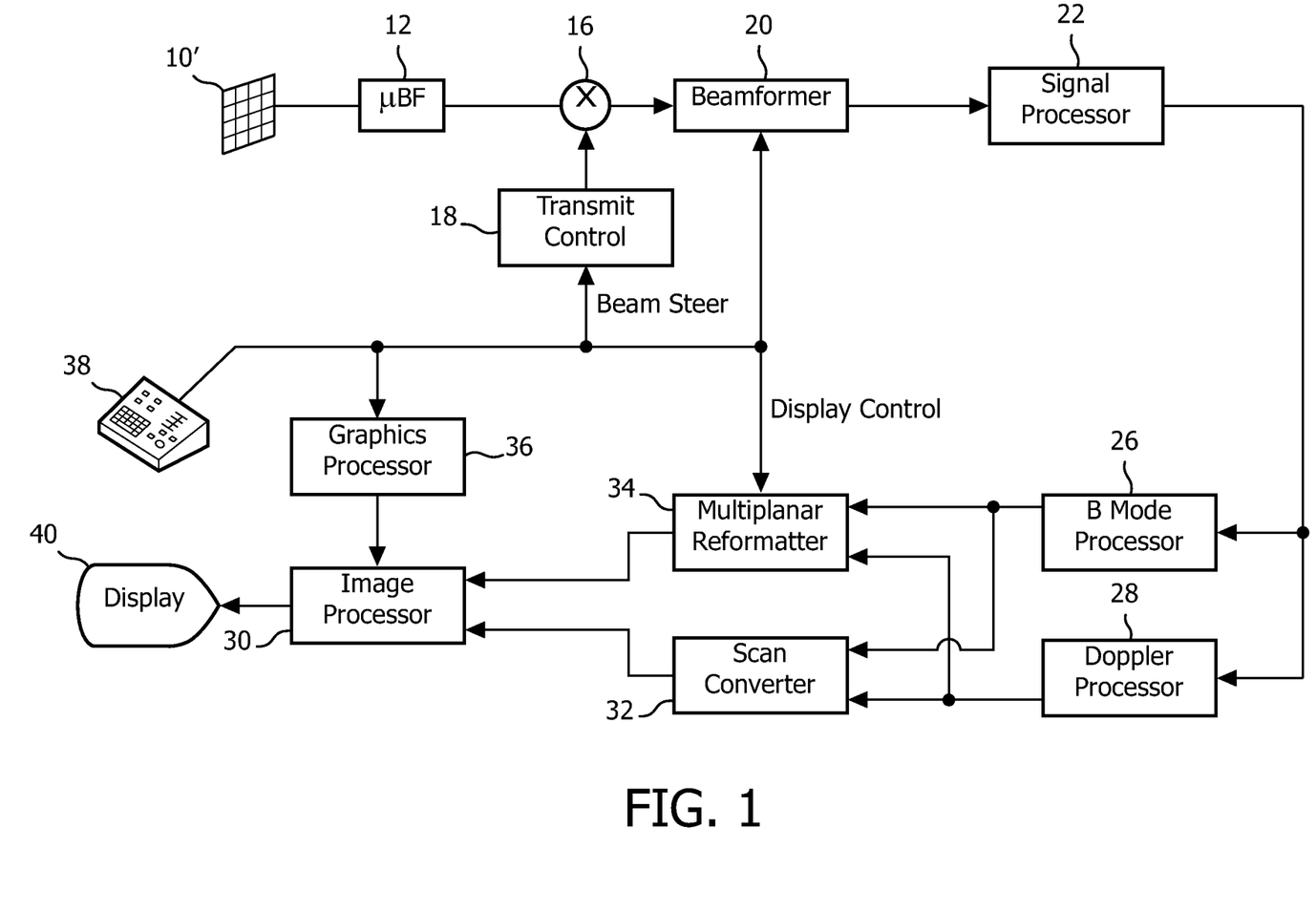
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. In FIG. 1 a transducer array 10' is provided in an ultrasound probe 10 for transmitting ultrasonic waves and receiving echo information. The transducer array 10' is a two dimensional array of transducer elements capable of scanning in three dimensions for 3D imaging. The transducer array is coupled to a microbeamformer 12 in the probe which controls transmission and reception of signals by the array elements.

Microbeamformers are capable of at least partial beamforming of the signals received by groups or "patches" of transducer elements as described in U.S. Pat. Nos. 5,997,479 (Savord et al.), 6,013,032 (Savord), and 6,623,432 (Powers et al.) The microbeamformer is coupled by the probe cable to a transmit/receive (T/R) switch 16 which switches between transmission and reception and protects the main beamformer 20 from high energy transmit signals. The transmission of ultrasonic beams from the transducer array 10 under control of the microbeamformer 12 is directed by the transmit controller 18 coupled to the T/R switch and the beamformer 20, which receives input from the user's operation of the user interface or control panel 38. One of the functions controlled by the transmit controller is the direction in which beams are steered. Beams may be steered straight ahead from (orthogonal to) the transducer array, or at different angles for a wider field of view as described below.

The partially beamformed signals produced by the microbeamformer 12 are coupled to a main beamformer 20 where partially beamformed signals from the individual patches of elements are combined into a fully beamformed signal. For example, the main beamformer 20 may have 128 channels, each of which receives a partially beamformed signal from a patch of 12 transducer elements. In this way the signals received by over 1500 transducer elements of a two dimensional array can contribute efficiently to a single beamformed signal.

The beamformed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle removal, signal compounding, and noise elimination.

The processed signals are coupled to a B mode processor 26 and a Doppler processor 28. The B mode processor 26 employs amplitude detection for the imaging of structures in the body such as normal tissue, cysts, nerve fibers, and blood cells. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor processes temporally distinct signals from tissue and blood flow for the detection of motion of substances such as the flow of blood cells in the image field. The structural and motion signals produced by these processors are coupled to a scan converter 32 and a multiplanar reformatter 34, which produce image data of tissue structure, flow, or a combined image of both characteristics. The scan converter will convert echo signals with polar coordinates into image signals of the desired image format such as a sector image in Cartesian coordinates. The multiplanar reformatter will convert echoes which are received from points in a common plane in a volumetric region of the body into an ultrasonic image of that plane, as described in U.S. Pat. No. 6,443,896 (Detmer). A volume renderer (not shown) may also be employed to convert a the echo signals of a 3D data set into a projected 3D image as viewed from a given reference point as described in U.S. Pat. No. 6,530,885 (Entrekin et al.) The 2D or 3D images are coupled from the scan converter, multiplanar reformatter, and volume renderer (when used) to an image processor 30 for further enhancement, buffering and temporary storage for display on an image display 40.

A graphics processor 36 is also coupled to the image processor 30 which generates graphic overlays for displaying with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 10' and hence the images produced by the transducer array and the ultrasound system. The user interface is also coupled to the multiplanar reformatter 34 for selection and control of a display of multiple multiplanar reformatted (MPR) images in accordance with the present invention as described below.

Figure 2A:
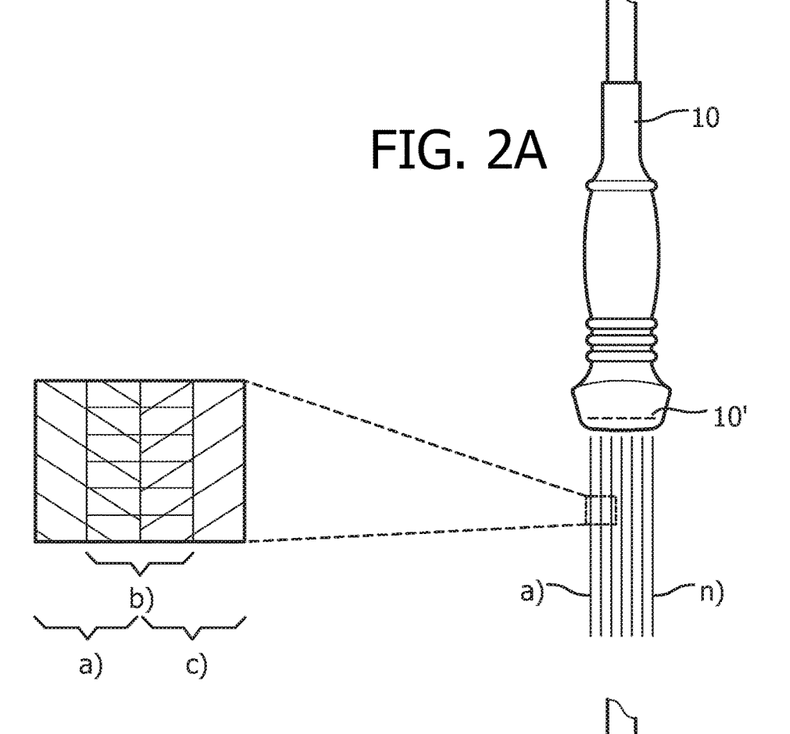
FIG. 2A illustrates different planar alignments which may be produced by an ultrasound probe of the present invention and overlapping thick slice image planes.
Figures 2B, 2C:
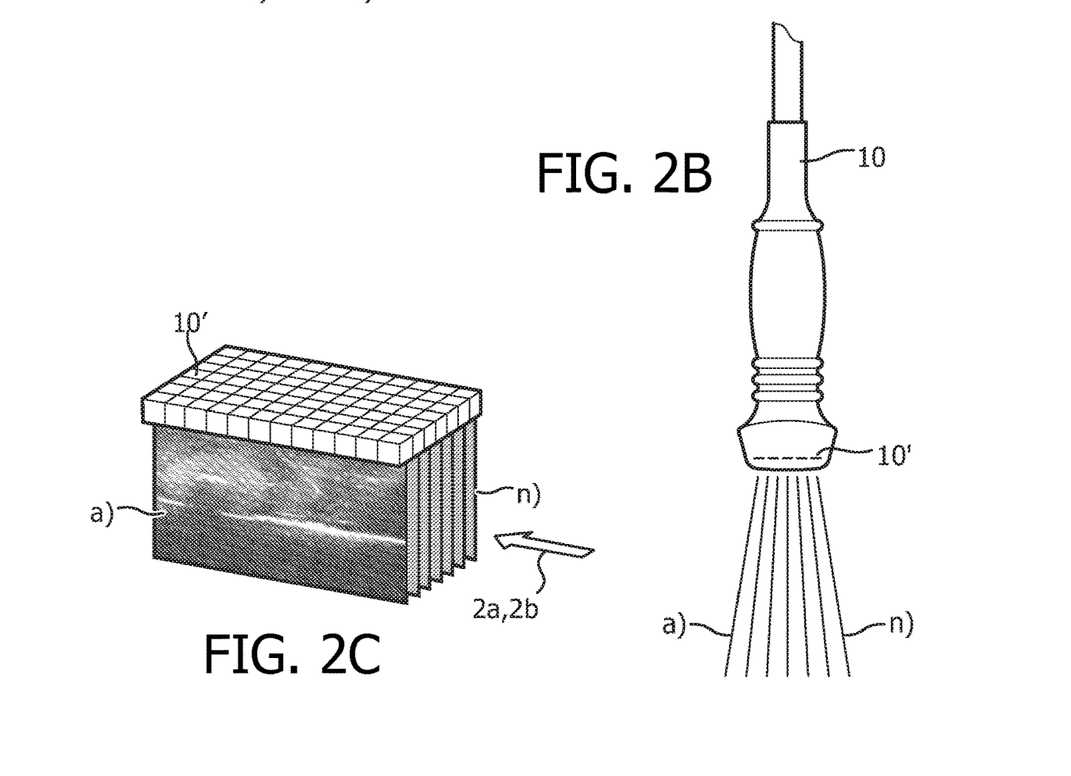
FIG. 2B illustrates different planar alignments which may be produced by an ultrasound probe of the present invention and overlapping thick slice image planes.
FIG. 2C illustrates spatial alignment in relation to a two dimentional array transducer.

In accordance with the principles of the present invention, the probe 10 scans a volumetric region in front of the two dimensional array transducer and the echoes received from scanning this 3D volume are arranged into images of spatially aligned 2D image planes as illustrated by FIGS. 2A-2C. Such a spatial alignment in relation to a two dimensional array transducer 10' is shown in FIG. 2C. In this drawing it is seen that the volume in front of (below in this illustration) the two dimensional array transducer 10' is scanned by beams of ultrasound and the echoes received in response to the beam transmission are arranged to form 2D images of a sequence of adjacent image planes identified as a) through n). In this example the multiplanar reformatter 34 has formatted a spatial sequence of parallel non-intersecting planes. These image planes a) through n) are shown "edge-on" (orthogonal to the plane of the drawing) in FIG. 2A, from the perspective of the arrow 2a,2b shown in association with FIG. 2C. The spacing and number of image planes are determined by the user and the type of array transducer used in the probe 10. There may be tens of image planes or scores of image planes, for instance. If the beams are closely spaced in the elevation dimension, closely spaced image planes can be formed and the number of planes over a given volume can be large. More widely spaced beams will produce more widely spaced image planes over the same dimension. The thickness of the image planes in the elevation dimension can be thin with tightly focused beams and the image planes can be slightly spaced apart from each other or contiguous. The image planes can also be overlapping in the thickness dimension as shown by the enlarged view to the left of FIG. 2A. In this example each image plane overlaps one-half of its adjacent image planes on each side, as shown by the brackets indicating the thickness of image planes a), b), and c). Image planes which overlap in thickness can be formed by overlapping "thick slice" images which are described in US Pat. pub. no. US2010/0168580 (Thiele).

FIG. 2B illustrates another sequence of image planes a) through n) which are scanned by a probe 10. In this example the non-intersecting planes are not perfectly parallel, but are slightly angled to diverge slightly from each other with increasing depth. This scan may be performed by steering the transmitted beams at the small angles offset from the orthogonal (normal) direction as this "edge-on" view of the image planes illustrates. These image planes will cover a wider field of view at increased depths than do the elevationally parallel planes of FIG. 2A, but with increased spacing between plane centers with increasing depth. When thick slice images are used in this technique the planes may be formed to overlap significantly in the near field but with decreasing overlap in the elevation direction with increasing depth.

The sequence of adjacent images, in either parallel planes or in angled image planes, can be formed in either of two ways in an embodiment of the present invention. One way is to direct the scanning beams in the desired image planes, then form each image from the echoes received from the beams which scan that plane. The other way is to acquire a 3D dataset of echo signals from points in the scanned volume, then use the multiplanar reformatter 34 to address and form an image of the echo data which is located in each desired plane. This addressing technique can form an image of a plane of any orientation through the 3D dataset by addressing and using only those datapoints which are located in a desired plane.

Figure 3:
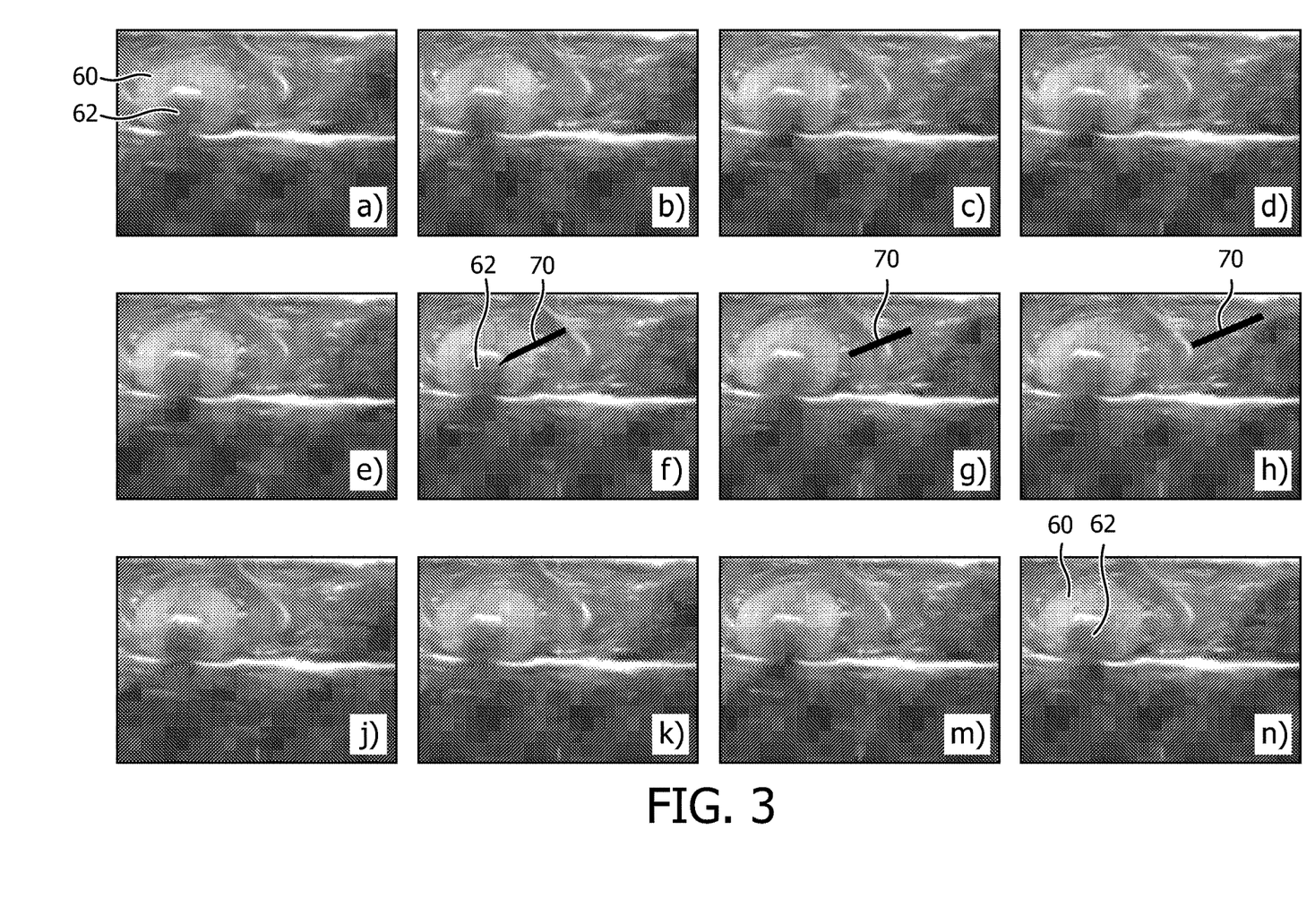
FIG. 3 illustrates a sequential display of spatially adjacent image planes of a needle in tissue in accordance with the principles of the present invention.

In accordance with the principles of the present invention, the adjacent image planes of the volumetric region formed by the multiplanar reformatter 34 are displayed in the sequence of their spatial order as illustrated by the ultrasound display of FIG. 3. As this example illustrates, the adjacent image planes are concurrently displayed. Each image plane is repetitively scanned in rapid succession so that each image in the display is a live, real-time image of its image plane. When the probe 10 is held against the body so that the target of an invasive procedure is within the field of view of the probe, the sequence of live images can be observed to guide a needle as it approaches and reaches the target site, and it is not necessary to maintain alignment of the needle with a single image plane. The progress of the needle insertion can be followed as it intersects successive image planes in the display. In the example of FIG. 3 the twelve images of adjacent image planes a) through n) show ultrasound images of the spine. The object of the procedure is to inject an anesthetic through a needle 70 into a nerve bundle 62 and to do so it is necessary to guide the insertion of the needle through the tissue of the body and cartilage 60 to reach the nerve bundle 62. A sequence of similar images may be seen in the case of a breast biopsy procedure, in which a fluid-filled cyst 60 surrounded by breast tissue contains a hard mass 62 at its core which it is desired to biopsy. The path of the needle as it approaches the nerve bundle 62 is not in alignment with a single image plane of the sequence. Instead, the needle 70 initially passes through image plane h) as it enters the body, then the angle of its insertion path passes through image plane g), and finally the needle reaches the target nerve bundle 62 in image plane f). In this example the needle will be seen to appear in image h), then image g), and then image f) in that order. When overlapping image planes are employed as shown in conjunction with FIG. 2a, adjacent images will contain some common image information. Thus, the same portion of the needle may appear in adjacent images. This is illustrated in FIG. 3, where some of the needle portion 70 of image g) is also seen in adjacent image f), and some of the needle portion of image g) is also seen in adjacent image h). This appearance of common image information will result in longer portions of the needle being visible in the images, affording improved needle visualization. The appearance of the needle 70 successively in these adjacent image planes gives the physician an intuitive sense of how the needle path is oriented with respect to the probe and hence where it is in the body and how it must be guided to reach the intended site of the procedure.

In a typical procedure a clinician will manipulate the probe 10 until the surgical site within the body is clearly in view, preferably in the center of the sequence of image planes, which would be images f) and g) in the example of FIG. 3. Alternately, the probe 10 may scan only a central image plane during this initial survey of the surgical site, then switch to the multiple MPR views when the procedure is started. The clinician will generally maneuver the probe in different orientations until the clinician finds what appears to be a good path for needle insertion in one of the images. This will generally be an intended needle insertion path which is aligned with one of the center images of the sequence. The clinician will usually prefer to follow the insertion of the needle in a single image, but the anatomy of the body may not readily accommodate this. The clinician will observe the position of the probe case or a marker on the case, which indicates the orientation of the image planes with respect to the probe position and, with or without the assistance of a needle guide, begin inserting the needle along the desired path. The needle may encounter harder and softer regions of tissue as it is inserted, causing the needle to vary from its intended path, even when the clinician is firmly guiding the needle. This change in direction can cause the needle to travel outside its single image plane in the elevation direction and into an adjacent plane. With a standard 2D imaging probe it is then necessary to adjust the position of the probe so that the entire needle, and particularly the needle tip is again in the image plane. It is also possible to move the two dimensional array probe 10 of the present example to realign the needle and its tip with a single image plane. But the present invention obviates this need to reposition the probe.

Once an optimal acoustic window is found on the skin of the body the probe can be kept in that position. It is not necessary to move the probe from its acoustic window as the needle path changes because the needle tip will appear in the image of an adjacent image plane, as illustrated by FIG. 3. Thus, the clinician can maintain the stationary position of the probe against the body, or even have an assistant hold the probe in position, while the clinician focuses attention on the sequential image display (FIG. 3) and guidance of the needle. It is no longer necessary to continually try to maneuver the needle insertion or the probe to keep the needle in a single image plane.

The ability to maneuver the probe 10 with one hand while inserting the needle with another enables the clinician to optimize visualization of the needle in the images. The visualization of the needle in the ultrasound images can be poor if the angle of incidence of the ultrasound beams and the needle is not optimal. If the needle is inserted at a shallow angle such that it is almost parallel to the skin surface and plane of the transducer, the needle will be virtually a specular reflector, returning strong echoes from the nearly-orthogonal transmit beams. But when the needle is inserted at a steep angle, the steepness of the angle of incidence will cause energy of the beams to, in effect, glance off of the needle and travel away from the probe; very little energy is then reflected back to the transducer array. The needle may thus be difficult to clearly visualize in the images. But without the need to maintain alignment of the needle path and a single image plane, the probe may be reoriented or angularly directed beams used as shown in FIG. 2b to better optimize the angle of incident of the beams and needle path so that stronger echo signals will be reflected from the needle back to the transducer array and a sharper image of the needle formed.

When the probe and system form a large number of adjacent MPR images, it may not be possible to view all of the images on the display at the same time. The clinician may want to view the images in larger size, for instance, the example of twelve images in FIG. 3, to be able to observe the images better. Thus, images a) through n) of FIG. 3 may only be images of the twelve central image planes produced by the probe. There may be additional adjacent images before image a) and after image n) in the full sequence of adjacent images. In this case, the clinician will adjust a display control of the user interface 38 to select the group of adjacent images to show on the display. Generally, the clinician will roll the sequence up or down as the insertion of the needle progresses, keeping the image of the current position of the needle tip, image f) in the example of FIG. 3, in the middle of the currently displayed group of images. By doing this the next adjacent image plane reached by the needle tip will always be currently displayed, either in the center row, or on the row above or below in the sequence.

Another display format which may be employed is to use a single row or column of adjacent images rather than multiple rows of images as illustrated in FIG. 3. The row of images will be of a portion of the full image sequence, and the clinician will slide the row left or right with a user control to bring new image planes on one side or the other of the currently displayed group into display. With such a display the clinician will generally slide the displayed images left or right to maintain the image displaying the tip of the needle in the center image of the row. The center image may be shown in a larger size than the others in the row to improve visualization of the needle tip in that image. The use of a single row will generally require more manipulation of the user control to slide the display left or right than will the multiple row display of FIG. 3.

An implementation of the present invention will often be preferred by clinicians who are familiar with invasive procedures guided by 2D ultrasound and are unaccustomed to using 3D volumetric imaging for surgical guidance, as the procedure can be guided by use of a sequence of only 2D images as shown in FIG. 3. The clinician gains the advantage of 3D since multiple planes in a 3D volumetric region are scanned, but does not need to observe 3D volumetric imaged to guide the procedure, but only familiar 2D images.

What is claimed is:

1. A method for guiding the insertion of an invasive instrument with an ultrasonic imaging system having a probe with a two-dimensional array transducer, the method comprising:
    following placement of the probe against an acoustic window of a body, transmitting ultrasound and receiving ultrasound echoes with the probe to ultrasonically image a site of an invasive procedure in a volumetric region of the body;
    forming a plurality of real-time two-dimensional (2D) images of adjacent planes of the volumetric region, each of the adjacent planes extending from the two-dimensional array transducer in a depth dimension to at least a depth of the invasive procedure site, wherein the adjacent planes of the volumetric region overlap one another in the thickness dimension by fifty percent;
    displaying concurrently the plurality of real-time 2D images of adjacent planes of the volumetric region in spatially adjacent order in a common display plane, wherein the plurality of real-time 2D images of adjacent planes of the volumetric region includes at least one image of the invasive procedure site; and
    updating the plurality of real-time 2D images of adjacent planes of the volumetric region during insertion of the invasive instrument into the volumetric region along an insertion path directed toward the invasive procedure site for observing the progress of instrument insertion as the instrument approaches the invasive procedure site and successively intersects a plurality of the adjacent planes of the volumetric region,
    wherein the updating includes concurrently displaying at least two of the plurality of real-time 2D images of adjacent planes of the volumetric region, each of the two of the plurality of real-time 2D images of adjacent planes of the volumetric region including a same portion of the invasive instrument when the insertion path is not aligned with a single plane of the adjacent planes of the volumetric region.

2. The method of claim 1, wherein forming comprises forming images of the adjacent planes of the volumetric region that are parallel in the depth dimension.

3. The method of claim 1, wherein forming comprises forming images of the adjacent planes of the volumetric region that are differently angled from one another in the depth dimension.

4. The method of claim 1, wherein forming comprises acquiring echo signals from points in the volumetric region to form a 3D dataset of echo data; and
    forming 2D images from echo data of the 3D dataset which are identified as being located in a common image plane to form a 2D image of at least one of the adjacent planes of the volumetric region.

5. The method of claim 4, wherein forming comprises forming the plurality of real-time two-dimensional (2D) images of adjacent planes of the volumetric region with a multiplanar reformatter.

6. The method of claim 1, further comprising manipulating the probe to obtain an improved angle of incidence between a direction of beams transmitted by the probe and the invasive instrument.

7. The method of claim 1, wherein displaying concurrently comprises displaying the plurality of real-time 2D images of adjacent planes of the volumetric region as a plurality of images in a plurality of rows,
    wherein an image plane of at least one image of the plurality of images of each of the plurality of rows is spatially adjacent to an image plane of an image of the plurality of images of another row of the plurality of rows.

8. The method of claim 7, wherein the plurality of images displayed in the plurality of rows comprise a subset of the plurality of real-time two-dimensional (2D) images of adjacent planes of the volumetric region; and
    further comprising using a user control to select a particular subset of images of the plurality of images displayed in the plurality of rows.

9. The method of claim 1, wherein displaying concurrently comprises displaying a single row of images of the plurality of real-time two-dimensional (2D) images of adjacent planes of the volumetric region.

10. The method of claim 9, wherein the single row of images comprise a subset of the plurality of real-time two-dimensional (2D) images of adjacent planes of the volumetric region; and
    further comprising using a user control to select a particular subset of images of the plurality of real-time two-dimensional (2D) images of adjacent planes of the volumetric region.

11. The method of claim 9, further comprising displaying one of the images in the single row of images in a larger display format than the other images.

12. A an ultrasonic imaging system comprising:
    a plurality of processors capable of executing instructions that cause the system to:

form a plurality of real-time two-dimensional (2D) images of adjacent planes of the volumetric region based on ultrasound echos received by a probe with a two-dimensional array transducer, each of the adjacent planes extending from the two-dimensional array transducer in a depth dimension to at least a depth of an invasive procedure site in the volumetric region of the body, wherein the adjacent planes of the volumetric region overlap one another in the thickness dimension by fifty percent;

display concurrently on a display the plurality of real-time 2D images of adjacent planes of the volumetric region in spatially adjacent order in a common display plane, wherein the plurality of real-time 2D images of adjacent planes of the volumetric region includes at least one image of the invasive procedure site; and update the plurality of real-time 2D images of adjacent planes of the volumetric region during insertion of the invasive instrument into the volumetric region along an insertion path directed toward the invasive procedure site for observing the progress of instrument insertion as the instrument approaches the invasive procedure site and successively intersects a plurality of the adjacent planes of the volumetric region, wherein the update includes concurrently displaying at least two of the plurality of real-time 2D images of adjacent planes of the volumetric region, each of the two of the plurality of real-time 2D images of adjacent planes of the volumetric region including a same portion of the invasive instrument when the insertion path is not aligned with a single plane of the adjacent planes of the volumetric region.

13. The system of claim 12, wherein the plurality of processors capable of executing instructions that further cause the system to form images of the adjacent planes of the volumetric region that are parallel in the depth dimension.

14. The system of claim 12, wherein the plurality of processors capable of executing instructions that further cause the system to form images of the adjacent planes of the volumetric region that are differently angled from one another in the depth dimension.

15. The system of claim 12, wherein the plurality of processors capable of executing instructions that further cause the system to:
   acquire echo signals from points in the volumetric region to form a 3D dataset of echo data; and
   form 2D images from echo data of the 3D dataset which are identified as being located in a common image plane to form a 2D image of at least one of the adjacent planes of the volumetric region.

16. The system of claim 15, wherein the plurality of processors capable of executing instructions that further cause the system to form the plurality of real-time two-dimensional (2D) images of adjacent planes of the volumetric region with a multiplanar reformatter.

17. The system of claim 12, wherein the plurality of processors capable of executing instructions that further cause the system to display the plurality of real-time 2D images of adjacent planes of the volumetric region as a plurality of images in a plurality of rows,
   wherein an image plane of at least one image of the plurality of images of each of the plurality of rows is spatially adjacent to an image plane of an image of the plurality of images of another row of the plurality of rows.

18. The system of claim 17, wherein the plurality of images displayed in the plurality of rows comprise a subset of the plurality of real-time two-dimensional (2D) images of adjacent planes of the volumetric region; and
   wherein the plurality of processors capable of executing instructions that further cause the system to receive a selected particular subset of images of the plurality of images displayed in the plurality of rows.

19. The system of claim 12, wherein the plurality of processors capable of executing instructions that further cause the system to display a single row of images of the plurality of real-time two-dimensional (2D) images of adjacent planes of the volumetric region.

20. The method of claim 19, wherein the plurality of processors capable of executing instructions that further cause the system to display one of the images in the single row of images in a larger display format than the other images.

21. A an ultrasonic imaging system comprising:
   a probe with a two-dimensional array transducer, the probe configured to transmit ultrasound and receive ultrasound echoes in a volumetric region of a body; and
   a plurality of processors capable of executing instructions that cause the system to:
   form a plurality of real-time two-dimensional (2D) images of adjacent planes of the volumetric region based on ultrasound echos received by the probe, each of the adjacent planes extending from the two-dimensional array transducer in a depth dimension to at least a depth of an invasive procedure site in the volumetric region of the body, wherein the adjacent planes of the volumetric region overlap one another in the thickness dimension by fifty percent;
   display concurrently on a display the plurality of real-time 2D images of adjacent planes of the volumetric region in spatially adjacent order in a common display plane, wherein the plurality of real-time 2D images of adjacent planes of the volumetric region includes at least one image of the invasive procedure site; and
   update the plurality of real-time 2D images of adjacent planes of the volumetric region during insertion of the invasive instrument into the volumetric region along an insertion path directed toward the invasive procedure site for observing the progress of instrument insertion as the instrument approaches the invasive procedure site and successively intersects a plurality of the adjacent planes of the volumetric region,
   wherein the update includes concurrently displaying at least two of the plurality of real-time 2D images of adjacent planes of the volumetric region, each of the two of the plurality of real-time 2D images of adjacent planes of the volumetric region including a same portion of the invasive instrument when the insertion path is not aligned with a single plane of the adjacent planes of the volumetric region.

22. The method of claim 1, further comprising receiving a manipulation of the probe to obtain an improved angle of incidence between a direction of beams transmitted by the probe and the invasive instrument.

* * * * *